United States Patent [19]
Halpern

[11] 3,993,560
[45] Nov. 23, 1976

[54] METHOD AND APPARATUS FOR MONITORING CELLULAR ACTIVITIES

[76] Inventor: Richard M. Halpern, 1125 Maytor Place, Beverly Hills, Calif. 90210

[22] Filed: Feb. 27, 1975

[21] Appl. No.: 553,502

[52] U.S. Cl. .............................. 210/94; 128/214 R; 195/127; 210/184; 210/321 B
[51] Int. Cl.² ........................................ B01D 31/00
[58] Field of Search ................ 195/139, 127; 424/9; 210/321, 22, 94, 184; 128/214 R, DIG. 3

[56] References Cited
UNITED STATES PATENTS

| | | | |
|---|---|---|---|
| 3,062,737 | 11/1962 | Azurlosa et al. | 210/22 |
| 3,228,876 | 1/1966 | Mahon | 210/22 |
| 3,459,176 | 8/1969 | Leonard | 210/321 X |
| 3,483,867 | 12/1969 | Markovitz | 210/321 X |
| 3,821,087 | 6/1974 | Knazek et al. | 195/139 X |

*Primary Examiner*—Frank A. Spear, Jr.
*Attorney, Agent, or Firm*—Ralph B. Pastoriza

[57] ABSTRACT

A method and means are provided for observing and recording by time lapse photography the growth of cells such as cancer cells outside the human body while nourishing the cells with human blood so that the situation simulates the actual cell growth within the body. The patient's blood is circulated through an extra corporeal chamber by an arteriovenous shunt, the tissue cells to be monitored being disposed in the chamber under a controlled environment. The chamber has transparent top and bottom covers so that the growing tissue may be properly illuminated by a light source and time lapse photographs taken.

2 Claims, 3 Drawing Figures

METHOD AND APPARATUS FOR MONITORING CELLULAR ACTIVITIES

This invention relates generally to the examination and monitoring of tissue cultures and more particularly to an improved method and apparatus for monitoring cellular activities in a patient's tissue outside of the patient's body.

BACKGROUND OF THE INVENTION

Tissue culture experiments are usually carried out by placing tissue cells in a culture flask within a suitable medium and adding suitable chemicals while observing cellular activity and growth. It is not uncommon to take time lapse photographs through the culture flasks to make a permanent record of growth.

The major problem with the foregoing procedure is a consequence of the fact that the medium in the flask has to be changed as often as three or four days. As a consequence, the field one is photographing is therefore often changed. It is evident that improved results could be realized if the cellular growth could be recorded over an extended period of time, substantially longer than three or four days with substantially the same background and environment.

In addition to the above, studying the cellular activities in a tissue culture from a given patient does not provide the same information as would be obtained if the cellular activity could be examined while growth is taking place in the patient's body. In this latter event, the effects of any chemotherapeutic regimen on the patient's own tumor cells could readily be monitored.

At the present time, approximately only five per cent (5%) of all tumors of human origin can be cultivated and examined.

BRIEF DESCRIPTION OF THE PRESENT INVENTION

With the foregoing in mind, the present invention contemplates a method of monitoring cellular activities in a tissue culture from a given patient including the steps of, first holding the particular cells in a given extra-corporeal controlled environment such as a suitable temperature controlled chamber having transparent top and bottom covers for easy visual examination of the interior of the chamber. Next, blood from the patient is circulated through the chamber to nourish the tissue and remove waste matter; that is, catabolic products formed by the culture cells. Finally, the cellular activities in the tissue can be readily recorded over an extended period of time while the culture cells are growing. Because of the circulation of blood there is no need to disturb the culture every three or four days.

The apparatus in the form of the chamber for carrying out the method includes inlet and outlet valve means for connection respectively to the patient's artery and vein and preferably also includes branch valve means for introducing various chemicals to the circulating blood passing through the chamber as well as other orifices to add or remove cells from the chamber. The continuous supply of nutrients and removal of waste products without having to reposition or remove the chamber from the photographic stage or otherwise disturb the growing cells is accomplished by the use of a bundle of hollow dialyzing fibers connecting the inlet valve means to the outlet valve means within the chamber.

BRIEF DESCRIPTION OF THE DRAWINGS

A better understanding of this invention will be had by now referring to the accompanying drawings in which.

DETAILED DESCRIPTION OF THE INVENTION

Figure 1:
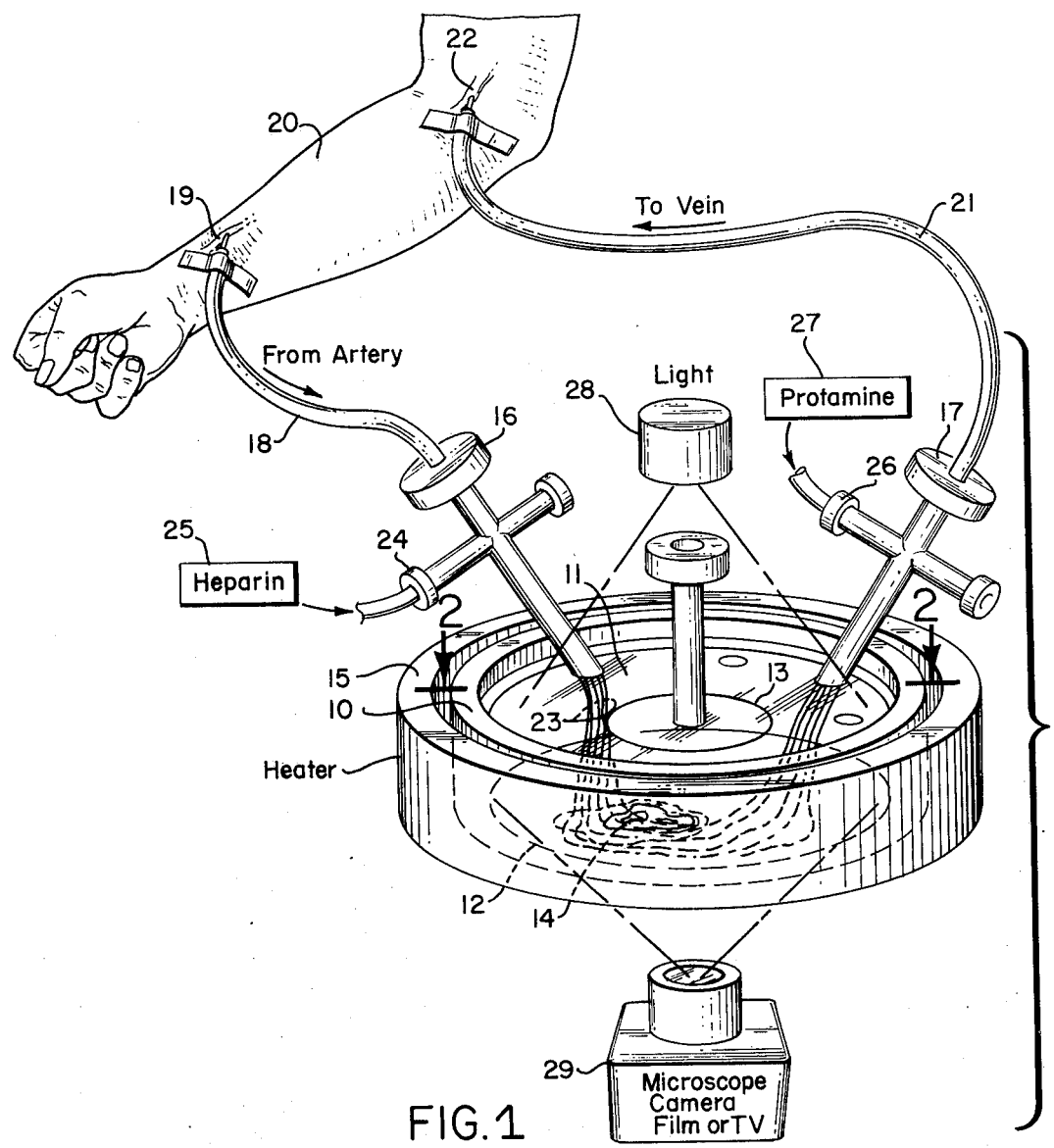
FIG. 1 is a perspective view partly diagrammatic in form illustrating the basic apparatus for monitoring cellular activities in tissue taken from a given patient.

Referring to FIG. 1, there is shown a closed sterile chamber 10 which may be formed from stainless steel or plexiglass provided with transparent top and bottom covers 11 and 12, so that the interior of the chamber can be viewed from above and below. As shown, the top cover 11 includes an access opening 13 normally closed by a similar transparent cover such that a tissue culture indicated in dotted lines at 14 may be received and positioned within the chamber.

The chamber is of a size and so designed that it can be maintained in a sterile condition by placing the chamber in a (10%) solution of formalin or a (70%) solution of ethonal. Further, the chamber is designed such that its interior volume is sufficiently large so that cells can grow for several days without overcrowding. A suitable volume would be in the range of from 10 to 20 milliliters.

Also illustrated in FIG. 1 is a heating means in the form of an annular ring structure 15 within which the chamber 10 may be positioned so that a thermostatically controlled temperature can be maintained in the interior of the chamber. The annular heating means is designed so as not to interfere with observation of the tissue culture 14 within the chamber either through the top or bottom transparent covers.

In order to continuously supply nutrients and remove waste products from the cells in the tissue culture, without having to move the chamber or otherwise disturb the growing cells, there is provided an inlet valve means 16 adjacent to one edge of the top surface 11 of the chamber and an outlet valve means 17 adjacent to another edge of the top surface of the chamber. As indicated in FIG. 1, the inlet valve means is connected as by a suitable tubing 18 directly to an artery 19 from a portion of the patient, such as his arm 20. The outlet valve means 17 in turn is connected as by tubing 21 to a patient's vein 22 on his arm 20.

The foregoing shunt is similar to the external arterio venous shunt extending from an artery to the inlet and a similar attachment of the outlet for the return flow to the patient's vein as is presently used for "artificial kidney" renal dialysis.

Filter means in the form of a bundle of hollow dialyzing fibers 23 in the chamber 10 connect the inlet valve means to the outlet valve means as shown in FIG. 1. Suitable nutrients are provided to the cells in the tissue 14 through the walls of the fibers 23 and waste products similarly are removed by flow from the tissue to the fibers.

In addition to the foregoing features described, in the preferred embodiment illustrated the inlet valve means includes an additional branch valve 24 permitting the introduction of various chemicals into the inlet valve and thus into the incoming blood flow. For example, one such chemical might be heparin, indicated at 25 to prevent blood clotting within the chamber. Similarly, the outlet valve means 17 may include a branch valve 26 for enabling the introduction of chemicals to the blood flowing back into the patient's vein. Such a drug might constitute protamine indicated at 27 to neutralize the effect of the anti-coagulant introduced by the heparin prior to the blood returning to the patient's body. Other chemicals may be simultaneously or alternatively introduced through additional branch valve structures shown in the inlet and outlet valve means.

The overall apparatus is completed by the provision of a light source 28 disposed above the chamber 10 for illuminating the tissue culture within the chamber through the transparent top cover 11, and a time lapse photographic camera or microscope symbolically illustrated at 29 below the bottom transparent cover 12. With this arrangement, the cellular activity can be continuously visually monitored and in addition, a succession of pictures at fixed time intervals may be taken to record the cellular growth.

Figure 2:
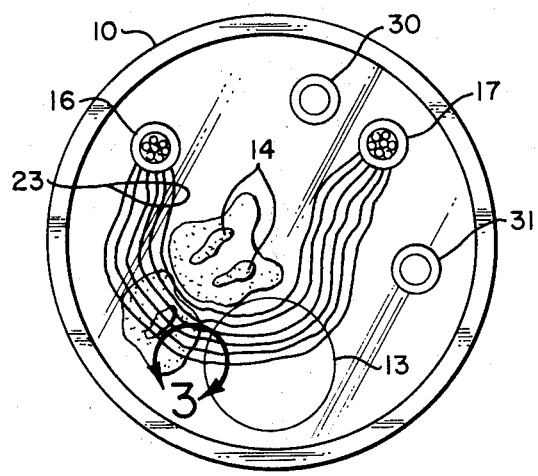
FIG. 2 is a cross section taken in the direction of the arrows 2—2 of FIG. 1; and, FIG. 3 is a greatly enlarged fragmentary view of the portion enclosed within the circular arrow 3 of FIG. 2.

FIG. 2 illustrates the bundle of fibers 23 connected between the inlet 16 and outlet 17 in somewhat greater detail wherein it will be noted that the fibers are in a slack condition distributed over a substantial area of the bottom of the chamber 10 adjacent to and intermingled with the tissue culture 14. Two or more outlets 30 and 31 in the chamber also provide means of removing or adding other cells to the tissue culture.

Figure 3:
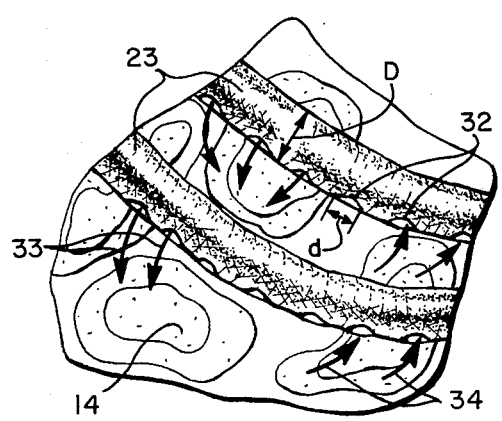

FIG. 3 shows in greatly exaggerated form two of the fibers 23 of FIG. 2 wherein it will be noted that there are small openings 32 in the side walls of each of the fibers or tubes. The particular dialyzing fibers illustrated may be obtained from Dow Chemical Company and normally have a diameter D of the order of 30 to 40 microns. The small openings 30 on the other hand are presently available in two diameter sizes $d$ sufficient to permit, respectively, transit of molecules less than 30,000 and 80,000 molecular weight. However, the size of these openings may be changed to permit longer molecule (antibodies) and other macromolecules to gain access to the confined chamber.

In FIG. 3, the arrows 31 represent blood nutrients nourishing the cells in the tissue 14 while the arrows 32 indicate the removal of metabolic waste products from the tissue.

OPERATION

In operation, a tissue or tumor to be examined and monitored is placed in the chamber 10 through the access opening 13 and the chamber itself placed within the heater 15 to assure that a proper controlled temperature within the chamber will be maintained. The inlet and outlet tubes 18 and 19 are connected respectively to an artery and vein in the patient's arm 20 all as described heretofore so that blood will circulate through the chamber and nourish the tissue as well as remove waste products therefrom, all in a continuous manner. As described heretofore, heparin and protamine may be introduced to the circulating blood to avoid coagulation in the chamber.

The particular tumor or other tissue to be examined can be grown over an extended period of time, there being no requirement to change the medium in the chamber. Moreover, time lapse photographs can be taken with a mechanism 29 as desired or taped by a TV camera. Furthermore, a second chamber or multiple chamber each with different kinds of cells could be placed in series with the first and also studied.

From the foregoing, it will be evident that a device is provided in which the patient's own blood can supply the nutrients and clear the chamber of any excretory products. The device also provides a means of studying the cells of a patient extra corporeally while subjecting the patient to various therapeutic regimens. Any tissue can correspondingly be studied in this manner. Particularly significant is the use of such a device to monitor the effects of any chemo-therapeutic regimen on the patient's own tumor cells. The apparatus also will enable one to cultivate extra-corporeally almost all tumors of human origin.

While a particular embodiment of apparatus for carrying out the method has been set forth and described, it should be understood that variations in the apparatus provided can be effected without departing from the scope and spirit of the invention.

What is claimed is:
1. An apparatus for monitoring cellular activities in tissue to be examined from a given patient including in combination:
   a. a closed sterile chamber for holding said tissue culture having transparent top and bottom covers so that the interior of the chamber can be viewed from above and below said chamber having an access opening for receiving said tissue culture;
   b. annular heating means surrounding said chamber in a manner so as not to interfere with observation of the interior of the chamber through said top and bottom covers and provide a controlled temperature in said chamber;
   c. inlet valve means adjacent to one edge of the top surface of the chamber for connection to said patient's artery and including a branch valve connecting means for introducing chemicals to blood entering said chamber;
   d. outlet valve means adjacent to another edge of the top surface of said chamber for connection to said patient's vein and including a branch valve connecting means for introducing other chemicls to the blood to neutralize the effect of said first mentioned chemicals prior to the blood returning to the patient; and
   e. filter means in the form of a bundle of hollow dialyzing fibers in said chamber connecting said inlet valve means to said outlet valve means, whereby said patient's blood may be continuously circulated through said filter means in said chamber to nourish cells in said tissue and remove metabolic waste products while visually monitoring cellular activities through said transparent covers.

2. An apparatus according to claim 1, including a light source positioned above said chamber and a time lapse photographic means positioned below said chamber for taking a succession of pictures of said tissue through said bottom transparent cover at fixed time intervals.

* * * * *